(12) United States Patent
Svensson

(10) Patent No.: US 6,589,965 B2
(45) Date of Patent: Jul. 8, 2003

(54) METHOD OF TREATING AND PREVENTING MIGRAINE HEADACHES

(75) Inventor: Kjell A. Svensson, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/999,251

(22) Filed: Nov. 1, 2001

(65) Prior Publication Data

US 2002/0091140 A1 Jul. 11, 2002

(51) Int. Cl.[7] .............................................. A61K 31/451
(52) U.S. Cl. ...................................................... 514/317
(58) Field of Search ................................ 514/317, 429, 514/331

(56) References Cited

FOREIGN PATENT DOCUMENTS

CA          1327364        *  3/1994

* cited by examiner

*Primary Examiner*—Phyllis G. Spivack
(74) *Attorney, Agent, or Firm*—Flynn, Thiel, Boutell & Tanis, P.C.

(57) ABSTRACT

A method of preventing or treating migraine headaches is disclosed comprising administering to a person in need thereof a pharmacologically effective amount of specific substituted phenylazacycloalkanes. These compounds can treat or prevent symptoms associated with migraine headaches and yet avoid undesirable side affects associated with conventional migraine treatment compositions. Additionally, other agents used to treat migraine headaches can be used in combination therewith.

24 Claims, 1 Drawing Sheet

METHOD OF TREATING AND PREVENTING MIGRAINE HEADACHES

FIELD OF THE INVENTION

The present invention is directed to a method for treating and preventing a migraine headache and other symptoms associated therewith using substituted phenylazacycloalkanes.

BACKGROUND OF THE INVENTION

Migraine is a common, debilitating disorder that affects approximately 15% of the adult population. There are two major types of migraines, migraine without aura, which occurs in 85% of migraineurs, and migraine with aura. It has been apothesized that the activation of dopamine receptors may be involved in the pathophysiology of migraines since many of the symptoms associated with migraines can be attributed to the stimulation of dopamine receptors. That is, nausea, vomiting, gastrokinetic changes, hypotension, and other autonomic nervous system changes are migraine symptoms that are consistent with the activation of dopaminergic neurotransmission. Additional evidence of dopamine receptor hypersensitivity in migraineurs has been demonstrated by the induction of yawning, nausea, vomiting, hypotension and other symptoms of a migraine attack by dopaminergic agonists at doses that do not effect non-migraineurs.

In light of these findings, a variety of dopamine antagonists have been used in the acute treatment of migraine headaches. In a study, haloperidol, a potent D2 dopamine receptor antagonist, completely or substantially relieved headache in six of six patients within 25–65 minutes after administration. Fisher, J Emerg Med, 1995; 13: 119–122. Prochlorperazine is another D2 dopamine receptor antagonist that has demonstrated a high degree of efficacy in the acute treatment of a migraine. In a prospective, randomized, double-blind clinical trial of Prochlorperazine, 74% of the patients had complete relief and an additional 14% had partial relief within 60 minutes of administration. Jones et al, JMA 1989; 261: 1174–1176. Domperidone which, because of its poor blood-brain barrier penetration properties, is considered to be a peripheral D2 dopamine receptor antagonist. Domperidone has been shown to prevent the occurrence of a migraine if taken during the prodromal phase of the disorder. Amery et al, Headache 1983; 23: 37–38. Chlorpromazine has been reported to be highly effective in the treatment of migraine patients in an emergency department with moderate drowsiness as a common side affect. Lane et al, Headache 1985; 25: 302–304. Flunarizine is a compound which displays significant dopamine antagonist properties and a moderate degree of affinity for the D2 dopamine receptor. In studies, intravenous Flunarizine provided a high degree of relief in the acute treatment of migraine, with the highest response rate being observed in patients with "classical migraine". Soyaka et al, Headache 1989; 29: 21–27. Metoclopramide is a non-phenothiazine D2 dopamine receptor antagonist having a relatively low affinity for the D2 receptor and is commonly used in Europe in the treatment of migraine where it is usually an adjunct medication to improve the absorption of concurrent oral analgesics. Ellis et al, Ann Emerg Med 1993; 22: 191–195. Additionally, Metoclopramide has been shown to have a beneficial effect when given prophylactically to individuals with migraine. Practitioner 1974; 212: 887–890. Nearly all experienced clinicians have recommended the use of dopamine antagonists in combination with other agents in the treatment of migraine. Lance, Headache, Ann Neurol 1981; 10: 1–10. However, a common problem with these dopamine antagonists is that they have potential central nervous system side affects when given in higher doses.

Substituted phenylazacycloalkanes are disclosed in U.S. Pat. Nos. 5,462,947 and 5,594,024 to Svensson et al which possess selective dopamine receptor pharmacological properties and are useful in treating central nervous system disorders such as depression symptoms, geriatric disorders, schizophrenia, narcolepsy, MBD, obesity, disturbances of sexual function and rehabilitation of drug abusers. However, there is no disclosure in this reference that the substituted phenylazacycloalkanes can be used in the treatment of migraines.

SUMMARY OF THE INVENTION

The present invention is directed to a method of preventing the occurrence of migraine headaches and symptoms associated with migraine headaches in a person susceptible to the migraine headaches which comprises a step of administering to the person a pharmacologically effective amount of a compound of formula (I) or a pharmaceutically acceptable salt thereof,

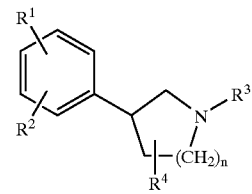

wherein n is 1 or 2; $R^1$ and $R^2$ are independently H, provided that both are not H, —OH, CN, $CH_2CN$, 2- or 4-$CF_3$, $CH_2CF_3$, $CH_2CHF_2$, $CH=CF_2$, $(CH_2)_2CF_3$, ethenyl, 2-propenyl, $OSO_2CH_3$, $OSO_2CF_3$, $SSO_2CF_3$, COR, COOR, $CON(R)_2$, $CONH_2$, $SO_xCH_3$, $SO_xCF_3$, $O(CH_2)_xCF_3$, where x is 0–2, $SO_2N(R)_2$, CH=NOR, COCOOR, $COCOON(R)_2$, $C_{1-8}$ alkyls, $C_{3-8}$ cycloalkyls, $CH_2OR$, $CH_2(R)_2$, $NRSO_2CF_3$, $NO_2$, halogen, phenyl in positions 2, 3 or 4, thienyl, furyl, pyrrole, oxazole, thiazole, N-pyrroline, triazole, tetrazole or pyridine;

$R^3$ is hydrogen, $CF_3$, $CH_2CF_3$, $C_{1-8}$ alkyl, $C_{3-8}$ cycloalkyl, $C_{4-9}$ cycloalkyl-methyl, $C_{2-8}$ alkenyl, $C_{2-8}$ alkynyl, 3,3,3-trifluoropropyl, 4,4,4-trifluorobutyl, —$(CH_2)_m$—$R^5$, where m is 1–8, $CH_2SCH_3$ or a $C_{4-8}$ alkyl bonded to the N-atom and one of its adjacent carbon atoms to form a heterocyclic structure;

$R^4$ and R are independently selected from hydrogen, $CF_3$, $CH_2CF_3$, $C_1$–$C_8$ alkyl, $C_{3-8}$ cycloalkyl, $C_{4-9}$ cycloalkyl-methyl, $C_{2-8}$ alkenyl, $C_{2-8}$ alkynyl, 3,3,3-trifluoropropyl, 4,4,4-trifluorobutyl, or —$(CH_2)_m$—$R^5$, where m is 1–8;

$R^5$ is phenyl, phenyl substituted with CN, $CF_3$, $CH_2CF_3$, $C_{1-8}$ alkyl, $C_{3-8}$ cycloalkyl, $C_{4-9}$ cycloalkyl-methyl, $C_{2-8}$ alkenyl or $C_{2-8}$ alkynyl, 2-thiophenyl, 3-thiophenyl, —$NR^6CONR^6R^7$ or $CONR^6R^7$; and $R^6$ and $R^7$ are independently hydrogen, $C_{1-8}$ alkyl, $C_{3-8}$ cycloalkyl, $C_{4-9}$ cycloalkyl-methyl, $C_{2-8}$ alkenyl or $C_{2-8}$ alkynyl.

Another embodiment of the present invention is directed to a method of treating a migraine headache and symptoms associated therewith in a person having a migraine headache attack comprising a step of administering to said person a pharmacologically effective amount of the compound of formula (I), or a pharmaceutically acceptable salt thereof.

In a preferred embodiment, the compound of formula (I) is S-(−)-3-[3-(methylsulfonyl)phenyl]-1-propyl-piperidine. The substituted phenylazacycloalkanes used in the present invention can be in the form of both racemic mixtures and pure enantiomers (R or S) but the preferred compounds have the S absolute configuration, according to the Cahn-Ingold-Prelog priority rules. Depending on the N-substituent, some of these S-enantiomers are dextrorotatory while others are levorotatory. The compounds can also be provided in the form of a pharmaceutically acceptable salt, such as a hydrochloride salt.

The present invention provides a method for preventing and treating the occurrence of migraine headaches and symptoms associated therewith through the use of substituted phenylazacycloalkane compounds without inducing the side affects associated with other dopamine antagonists. In the present invention, the substituted phenylazacycloalkanes can be administered concomittently with other medications used for the prevention and treatment of migraines.

DETAILED DESCRIPTION OF THE INVENTION

Figure 1:
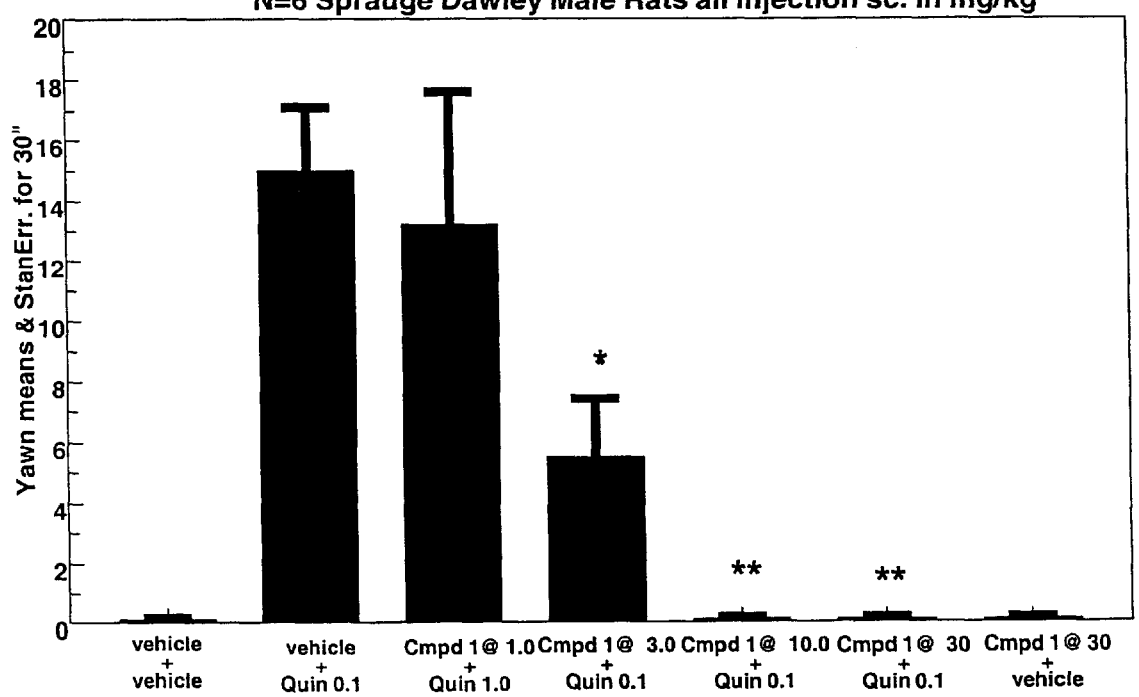
FIG. 1 illustrates the antagonism of quinpirole-induced yawning in rats by S-(−)-3-[3-(methylsulfonyl)phenyl]-1-propyl-piperidine, indicated as "Cmpd 1".

The substituted phenylazacycloalkane derivatives and their method of preparation are disclosed in U.S. Pat. Nos. 5,462,947 and 5,594,024 to Svensson et al and the disclosures of these patents are hereby incorporated by reference thereto in the present application.

As discussed previously, the substituted phenylazacycloalkane compounds of formula (I) are used to treat and prevent recurrence of migraine headaches and symptoms associated therewith in a person susceptible to migraines. The symptoms associated with migraines which can be treated by the present invention include yawning, nausea, vomiting, drowsiness, irritability, hyperactivity, hypertension, gastrokinetic dysfunction and hypotension among others. The daily dosage amount of the compound of formula (I) is from 0.5–2,000 mg. When the compound is administered orally, the daily dosage amount is from about 1–2,000 mg, with from 10–500 mg being preferred. If the compound of formula (I) is administered parenterally, the daily dosage amount is from about 0.5–1,000 mg with from 5 mg–250 mg being preferred. The compound of formula (I) can be administered as a single treatment or in combination with other agents used to treat migraines including analgesics such as acetyl-salicylic acid, anti-inflammatory agents such as NSAID's cox-2 inhibitors, ergotamines and triptan's such as sumatriptan, naritriptan and almotriptan. Other known migraine medications can be used in combination with the compounds of formula (I).

The compounds of formula (I) can be provided in both the racemic mixtures and the pure R or S enantiomers. The preferred compounds have the S absolute configuration according to the Cahn-Ingold-Prelog priority rules and, depending on the N-substituents, may be dextrorotatory or levorotatory. An especially preferred compound of formula (I) is S-(−)-3-[3-(methylsulfonyl)phenyl]-1-propyl-piperidine, which can be provided in the form of a pharmaceutically acceptable salt thereof, such as the hydrochloride salt.

The compounds of formula (I) can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15$^{th}$ Ed., 1975). The compounds and compositions of the present invention can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. The above listing is merely representative and one skilled in the art could envision other binders, excipients, sweetening agents and the like. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices including, but not limited to, those relying on osmotic pressures to obtain a desired release profile (e.g., the OROS drug delivery devices as designed and developed by Alza Corporation).

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions. Sterilization of the powders may also be accomplished through irradiation and aseptic crystallization methods. The sterilization method selected is the choice of the skilled artisan.

Yawning is a behavior that has been linked to activation of dopaminergic neurotransmission. Therefore, the blockage of quinpirole-induced yawning in rats has been used as an animal model to study the potential antagonism of migraine symptoms.

EXAMPLE

Male Sprague Dawley Rats were used in this example. The animals were allowed 12 day acclimatization before testing and at the time of the study, their body weights ranged from 280–330 grams. The rats were housed in standard size steel cages with four animals per cage and were maintained on a 12 hour light/dark schedule with the lights being on from 6:00 a.m. to 6:00 p.m. All tests were performed between 8:00 a.m. and 2:00 p.m. Six animals were used per group.

S-(−)-3-[3-(methylsulfonyl)phenyl]-1-propyl-piperidine in an amount of 10 or 30 mg/kg in a saline vehicle or the vehicle per se was injected 15 minutes before the dopamine D2 agonist quinpirole in an amount of 0.1 mg/kg in a saline vehicle or the saline vehicle per se was administered to the animals. The animals were then placed individually in a 6"×6"plexiglass observation cages and the number of yawns were counted for the subsequent 30 minutes. The results are shown in FIG. 1 with the data being expressed as the mean total number of yawns per 30 minutes. An analysis of variance was used for statistical calculations and probability levels of <0.05 was regarded as being statistically significant.

The dopamine D2 agonist quinpirole produced an average of 13–15 yawns per 30 minutes while no yawning behavior was observed in the vehicle treated animals. (S-(S) -3-[3-(methylsulfonyl)phenyl]-1-propyl-piperidine, indicated as "Cmpd 1" in FIG. 1, produced a dose-dependent and complete antagonism of the yawning behavior induced by quinpirole. Additionally, this compound given alone at a dose of 30 mg/kg failed to induce yawning behavior. Since yawning is part of a behavioral syndrome occurring in most patients during a migraine attack, the present method can be used in the prevention and the treatment of migraine and symptoms associated therewith.

What is claimed is:

1. A method of preventing the occurrence of migraine headaches and symptoms associated with migraine headaches in a person susceptible to said migraine headaches comprising the step of administering to said person a pharmacologically effective amount of a compound of formula (I), or a pharmaceutically acceptable salt thereof,

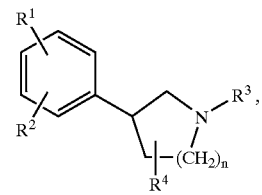

wherein
n is 2;
$R^1$ and $R^2$ are independently H, provided that both are not H, —OH, CN, $CH_2CN$, 2- or 4-$CF_3$, $CH_2CF_3$, $CH_2CHF_2$, $CH=CF_2$, $(CH_2)_2CF_3$, ethenyl, 2-propenyl, $OSO_2CH_3$, $OSO_2CF_3$, $SSO_2CF_3$, COR, COOR, $CON(R)_2$, $CONH_2$, $SO_xCH_3$, $SO_xCF_3$, $O(CH_2)_xCF_3$, where x is 0–2, $SO_2N(R)_2$, CH=NOR, COCOOR, $COCOON(R)_2$, $C_{1-8}$ alkyl, $C_{3-8}$ cycloalkyl, $CH_2OR$, $NO_2$, halogen, thienyl, furyl, pyrrole, oxazole, thiazole, N-pyrroline, triazole, tetrazole or pyridine;
$R_3$ is hydrogen, $CF_3$, $CH_2CF_3$, $C_{1-8}$ alkyl, $C_{3-8}$ cycloalkyl, $C_{4-9}$ cycloalkyl-methyl, $C_{2-8}$ alkenyl, $C_{2-8}$ alkynyl, 3,3,3-trifluoropropyl, 4,4,4-trifluorobutyl, —$(CH_2)_m$—$R^5$, where m is 1–8, $CH_2SCH_3$ or a $C_{4-8}$ alkyl bonded to the N-atom and one of its adjacent carbon atoms to form a heterocyclic structure;
$R^4$ and R are independently selected from hydrogen, $CF_3$, $CH_2CF_3$, $C_1$–$C_8$ alkyl, $C_{3-8}$ cycloalkyl, $C_{4-9}$ cycloalkyl-methyl, $C_{2-8}$ alkenyl, $C_{2-8}$ alkynyl, 3,3,3-trifluoropropyl, 4,4,4-trifluorobutyl, or —$(CH_2)_m$—$R^5$, where m is 1–8;
$R^5$ is phenyl, phenyl substituted with CN, $CF_3$, $CH_2CF_3$, $C_{1-8}$ alkyl, $C_{3-8}$ cycloalkyl, $C_{4-9}$ cycloalkylmethyl, $C_{2-8}$ alkenyl or $C_{2-8}$ alkynyl, 2-thiophenyl, 3-thiophenyl, —$NR^6CONR^6R^7$ or $CONR^6R^7$; and
$R^6$ and $R^7$ are independently hydrogen, $C_{1-8}$ alkyl, $C_{3-8}$ cycloalkyl, $C_{4-9}$ cycloalkyl-methyl, $C_{2-8}$ alkenyl or $C_{2-8}$ alkynyl.

2. The method of claim 1, wherein said compound of formula (I) is S-(−)-3-[3-(methylsulfonyl)phenyl]-1-propyl-piperidine.

3. The method of claim 1, additionally comprising the step of administering at least one member selected from the group consisting of an analgesic, an anti-inflammatory agent, an ergotamine and a triptan to said person.

4. The method of claim 1, wherein the compound of formula (I) is administered in a daily amount of from 0.5–2000 mg.

5. The method of claim 4, wherein the compound of formula (I) is administered in a daily amount of from 5–500 mg.

6. The method of claim 1, wherein the symptoms are pain, yawning, drowsiness, mood changes, hypotension, nausea and vomiting.

7. The method of claim 1, wherein the compound of formula (I) is administered orally in a daily amount of 1–2000 mg.

8. The method of claim 7, wherein the daily amount is 10–500 mg.

9. The method of claim 1, wherein the compound of formula (I) is administered parenterally in a daily amount of 0.5–1000 mg.

10. The method of claim 9, wherein the daily amount is 5–250 mg.

11. The method of claim 1, wherein $R^1$ is H, $R^2$ is $SO_2CH_3$, $R^3$ is $C_{1-8}$ alkyl and $R_4$ is H.

12. The method of claim 1, wherein $R^1$ is H, $R^2$ is selected from the group consisting of $OSO_2CH_3$, $OSO_2CF_3$, $SSO_2CF_3$, $SO_xCH_3$, $SO_xCF_3$ and $SO_2N(R)_2$, $R^3$ is $C_{1-8}$ alkyl and $R^4$ is H.

13. A method of treating a migraine headache and symptoms associated with migraine headaches in a person having a migraine headache attack comprising the step of administering to said person a pharmacologically effective amount of a compound of formula (I), or a pharmaceutically acceptable salt thereof,

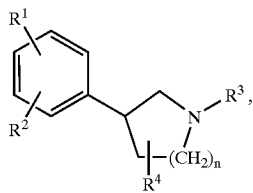

wherein n is 2;

$R^1$ and $R^2$ are independently H, provided that both are not H, —OH, CN, $CH_2CN$, 2- or 4-$CF_3$, $CH_2CF_3$, $CH_2CHF_2$, $CH=CF_2$, $(CH_2)_2CF_3$, ethenyl, 2-propenyl, $OSO_2CH_3$, $OSO_2CF_3$, $SSO_2CF_3$, OCR, COOR, $CON(R)_2$, $CONH_2$, $SOxCH3$, $SO_xCF_3$, $O(CH_2)_xCF_3$, where x is 0–2, $SO_2N(R)_2$, CH=NOR, COCOOR, $COCOON(R)_2$, $C_{1-8}$ alkyl, $C_{3-8}$ cycloalkyl, $CH_2OR$, $NO_2$, halogen, thienyl, furyl, pyrrole, oxazole, thiazole, N-pyrroline, triazole, tetrazole or pyridine;

$R^3$ is hydrogen, $CF_3$, $CH_2CF_3$, $C_{1-8}$ alkyl, $C_{3-8}$ cycloalkyl, $C_{4-9}$ cycloalkyl-methyl, $C_{2-8}$ alkenyl, $C_{2-8}$ alkynyl, 3,3,3-trifluoropropyl, 4,4,4-trifluorobutyl, —$(CH_2)_m$—$R^5$, where m is 1–8, $CH_2SCH_3$ or a $C_{4-8}$ alkyl bonded to the N-atom and one of its adjacent carbon atoms to form a heterocyclic structure;

$R^4$ and R are independently selected from hydrogen, $CF_3$, $CH_2CF_3$, $C_{1-8}$ alkyl, $C_{3-8}$ cycloalkyl, $C_{4-9}$ cycloalkyl-methyl, $C_{2-8}$ alkenyl, $C_{2-8}$ alkynyl, 3,3,3-trifluoropropyl, 4,4,4-trifluorobutyl, or —$(CH_2)_m$—$R^5$, where m is 1–8;

$R^5$ is phenyl, phenyl substituted with CN, $CF_3$, $CH_2CF_3$, $C_{1-8}$ alkyl, $C_{3-8}$ cycloalkyl, $C_{4-9}$ cycloalkyl-methyl, $C_{2-8}$ alkenyl or $C_{2-8}$ alkynyl, 2-thiophenyl, 3-thiophenyl, —$NR^6CONR^6R_7$ or $CONR^6R^7$; and $R^6$ and $R^7$ are independently hydrogen, $C_{1-8}$ alkyl, $C_{3-8}$ cycloalkyl, $C_{4-9}$ cycloalkyl-methyl, $C_{2-8}$ alkenyl or $C_{2-8}$ alkynyl.

14. The method of claim 13, wherein said compound of formula (I) is S-(−)-3-[3-(methylsulfonyl)phenyl]-1-propyl-piperidine.

15. The method of claim 13, additionally comprising the step of administering at least one member selected from the group consisting of an analgesic, an anti-inflammatory agent, an ergotamine and a triptan to said person.

16. The method of claim 13, wherein the compound of formula (I) is administered in a daily amount of from 0.5–2000 mg.

17. The method of claim 16, wherein the compound of formula (I) is administered in a daily amount of from 5–500 mg.

18. The method of claim 13, wherein the symptoms are pain, yawning, drowsiness, mood changes, hypotension, nausea and vomiting.

19. The method of claim 13, wherein the compound of formula (I) is administered orally in a daily amount of 1–2000 mg.

20. The method of claim 19, wherein the daily amount is 10–500 mg.

21. The method of claim 13, wherein the compound of formula (I) is administered parenterally in a daily amount of 0.5–1000 mg.

22. The method of claim 21, wherein the daily amount is 5–250 mg.

23. The method of claim 13, wherein $R^1$ is H, $R^2$ is $SO_2CH_3$, $R^3$ is $C_{1-8}$ alkyl and $R^2$ is H.

24. The method of claim 13, wherein $R^1$ is H, $R^2$ is selected from the group consisting of $OSO_2CH_3$, $OSO_2CF_3$, $SSO_2CF_3$, $SO_xCH_3$, $SO_xCF_3$ and $SO_2N(R)_2$, $R^3$ is $C_{1-8}$ alkyl and $R^4$ is H.

* * * * *

UNITED STATES PATENT AND TRADEMARK OFFICE
CERTIFICATE OF CORRECTION

PATENT NO.    : 6,589,965 B2
DATED         : July 8, 2003
INVENTOR(S)   : Kjell A. Svensson It is certified that error appears in the above-identified patent and that said Letters Patent is hereby corrected as shown below:

Title page,
Please add:
--                    Related U.S. Application Data
[60] Provisional application No. 60/245,967, filed on November 3, 2000 --.

Column 7,
Line 37, change "OCR" to -- COR --.

Column 8,
Line 9, change "-$NR^6CONR^6R_7$" to -- -$NR^6CONR^6R^7$--.
Line 43, change "and $R^2$ is H" to -- and $R^4$ is H --.

Signed and Sealed this

Fourth Day of May, 2004

JON W. DUDAS
*Acting Director of the United States Patent and Trademark Office*